United States Patent [19]

Belanger

[11] Patent Number: 4,662,376
[45] Date of Patent: May 5, 1987

[54] OBSTETRICAL INSTRUMENT FOR RUPTURING THE AMNIOTIC MEMBRANES

[76] Inventor: Rose-Ange Belanger, 1551 Hébert, Lasalle, Quebec, Canada, H8N 2M9

[21] Appl. No.: 739,465

[22] Filed: May 29, 1985

[51] Int. Cl.⁴ .................. A61B 17/42; A61D 1/08
[52] U.S. Cl. ........................... 128/361; 604/115; 604/22; 128/329 R
[58] Field of Search ............ 128/361, 329 R, 314, 128/305, 330; 604/115, 22

[56] References Cited

U.S. PATENT DOCUMENTS

| 101,027 | 9/1906 | Leonard . | |
|---|---|---|---|
| 3,410,269 | 11/1968 | Hovick . | |
| 3,533,411 | 10/1970 | McNight . | |
| 3,624,747 | 11/1971 | McNight . | |
| 3,685,509 | 8/1972 | Bentall | 604/115 |
| 3,882,849 | 5/1975 | Jamshidi | 128/329 R |
| 4,299,219 | 11/1981 | Norris, Jr. | 604/115 |

FOREIGN PATENT DOCUMENTS 1004939 2/1977 Canada .
1163518 3/1984 Canada .

Primary Examiner—Richard J. Apley
Assistant Examiner—H. Macey
Attorney, Agent, or Firm—Robic, Robic & Associates

[57] ABSTRACT

An obstetrical instrument for rupturing in a safe and easy manner the foetal membranes of a pregnant woman in order to release the amniotic fluid contained in these membranes. The instrument comprises an elongated tubular member preferably made of a semi-rigid plastic material, which member is adapted to be inserted into the woman's vagina until its front end is in contact with the foetal membranes to be ruptured. A piston manually actuatable by a rod extending outwardly of the tubular member through the rear end thereof is movably mounted inside this member to create, when actuated, a vacuum sufficient to draw to a certain extent the foetal membranes inside this tubular member. Piercing pins are provided inside the tubular member for rupturing the foetal membranes when these membranes are so drawn inside the member on actuation of the piston with the rod.

6 Claims, 4 Drawing Figures

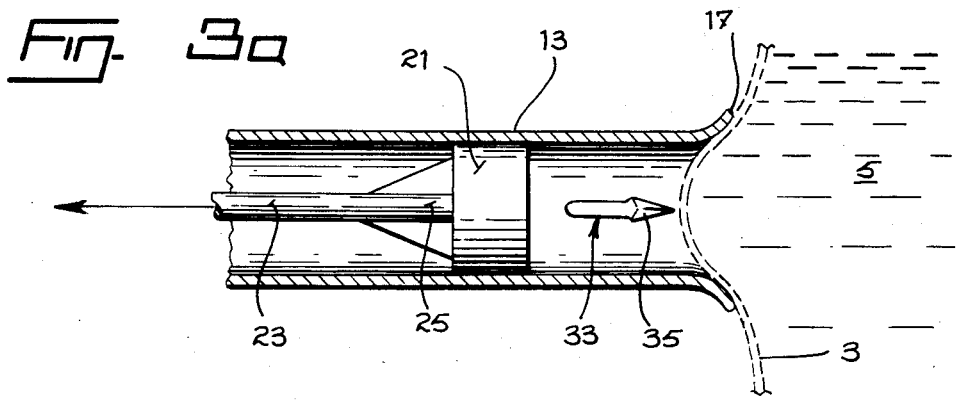
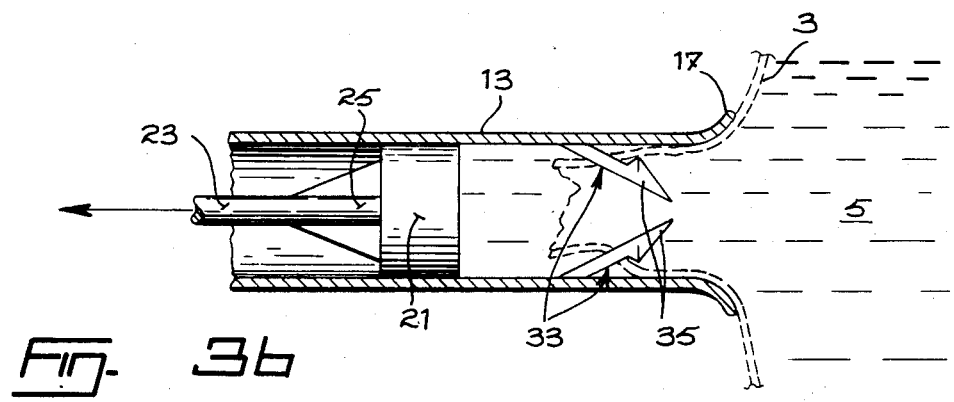

OBSTETRICAL INSTRUMENT FOR RUPTURING THE AMNIOTIC MEMBRANES

BACKGROUND OF THE INVENTION (a) Field of the invention

The present invention relates to an obstetrical instrument for use to rupture the foetal membranes of a pregnant woman in order to release the amniotic fluid trapped by these memboranes and thus to induce labour prematurely, to facilitate delivery and/or to reduce the internal pressure within the uterus.

(b) Background of the invention

Numerous instruments are known and commonly used by the obstetricians to rupture the foetal membranes of a pregnant woman for anyone of the above mentioned reason. By way of example, reference can be made to the instruments disclosed in U.S. Pat. No. 3,410,269 issued on Nov. 12, 1968 to J. H. Hovick and in U.S. Pat. Nos. 3,533,411 and 3,624,747 issued on Oct. 13, 1970 and Nov. 30, 1971 respectively both in the name of C. A. MaKnight and A. L. GILBERT.

The obstetrical instruments disclosed in these U.S. patents are rather efficient in practice, in addition of being easily suppliable in quantity and disposable form at a relatively low cost and in sterile condition. These known instruments are designed to reduce as much as possible the possibility of injuring the unborn foetus or damaging the mother's internal tissue. It should indeed be understood that this kind of instrument is used almost entirely by "feel", since the obstetrician cannot see the membranes to be ruptured nor the part of the instrument in contact with the membranes.

The problem with these known instruments is that they always have a sharp end with the sharp tip to puncture or rupture the membranes, even if this sharp end is retractable into a vaginal shielding body as disclosed in U.S. Pat. No. 3,410,263, or is in recess with respect to a blunt and nearly flat end surface as disclosed in U.S. Pat. Nos. 3,624,747 and 3,533,411.

SUMMARY OF THE INVENTION

An object of the present invention is to provide an obstetrical instrument for rupturing the foetal membranes of a pregnant woman in order to release the amniotic fluid contained within these membranes, which instrument is very simple in structure and much safer to use than any other similar instrument, while being inexpensive to manufacture in disposable form and sterile condition.

In accordance with the invention, this object is achieved with an obstetrical instrument for rupturing in a safe and easy manner the foetal membranes of a pregnant woman, which instrument comprises:

- an elongated tubular member having a front end and a rear end, this member being adapted to be inserted into the woman's vagina with the front end of the member in contact with the foetal membranes to be ruptured;
- a piston movably mounted inside the tubular member, this piston being tight enough to create, when actuated, a vacuum sufficient to draw to a certain extent the foetal membranes inside the tubular member;
- a rod for manually activating the piston, this rod having one end fixed to the piston and the other end extending outwardly of the tubular member at the rear end thereof; and
- means preferably consisting of the plurality of arrowhead shaped piercing pins, rigidly mounted in front of the piston and close to the front end of the member inside this member for rupturing the foetal membranes when these membranes are drawn inside the tubular member on actuation of the piston.

As can be easily understood, the piercing pins used for rupturing the membranes are not and can never be in direct contact with the unborn foetus not with the internal tissue of the mother, since these pins are located inside the tubular member and since only the elastic foetal membranes may be drawn by succion inside this member.

In order to facilitate introduction, actuation and more generally, manipulation of the instrument, the tubular member is preferably made of rigid or semi-rigid material and is slightly bent along its length to define a membrane contacting portion intertable into the woman's vagina and a handle portion extending at angle with respect to the membrane contacting portion. In this particular case, the piercing pins are located in the membrane contracting portion of the member and the front end of this member is slightly splayed to make contact with the membranes safer and more comfortable.

Holding means such as rings large enough to receive a finger, may be provided as the end of the rod extending out of the tubular member and onto the handle portion of this tubular member to facilitate their respective manipulation.

Although it makes use of a piston to create a vacuum in order to draw the foetal membranes inside the tubular member, the obstetricial instrument according to the invention is not as such. a surgical suction apparatus as those routinely used in surgical procedures for clearing a surgical wound of surgical debris such as blood, irrigation solution, fragment of certain hard tissues and the like (see, by way of example, Canadian patent No. 1,163,518). Also, the instrument according to the invention is not an endometrial sampler such as used by the obstetrician for the sampling or the biopsy of the internal uterine lining (see, for example, Canadian patent No. 1,004,939). The instrument according to the invention is exclusively a very specific instrument making use of very specific elements for a very specific object, namely rupturing the foetal membranes of a pregnant woman.

BRIEF DESCRIPTION OF THE DRAWINGS

A preferred embodiment of the invention will now be described in a non limitative manner with reference to the accompanying drawings wherein:

FIG. 3a and b are enlarged cross-sectional views of the front end of the instrument shown in FIGS. 1 and 2, when starting to draw the foetal membranes and when these foetal membranes are ruptured.

DESCRIPTION OF A PREFERRED EMBODIMENT OF THE INVENTION

Figure 1:
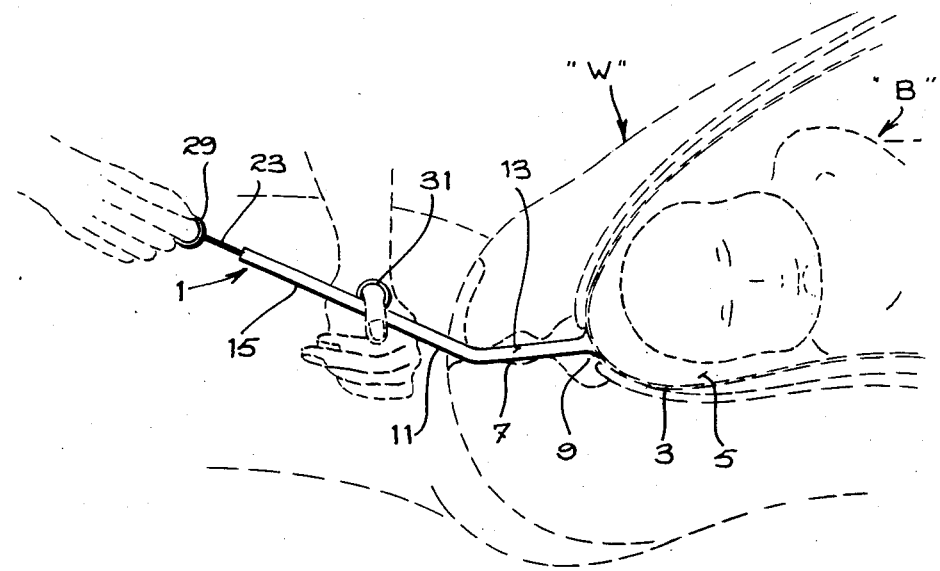
FIG. 1 is a cut-away view of a portion of the anatomy of a pregnant woman, showing an obstrical instrument according to the invention in use by an obstetrician to rupture the foetal membranes in order to release the amniotic fluid.

The obstetrical instrument 1 according to the invention as shown in the accompanying drawings is specifically intended to be used for rupturing the amnion and chorion membranes generally referred to as "foetal membranes" 3 of a woman W to release the amniotic fluid 5 surrounding an unborn baby B.

As explained hereinabove, the instrument 1 which is designed to rupture the membranes 3 in a very simple and efficient manner without any danger of injuring the unborn baby B or the internal tissue of the woman W, comprises a tubular member 11 having a membrane contacting portion 13 adapted in size and shape to be inserted into the woman's vagina 7 and the cervical canal 9 by the obstetrician in charge of the delivery.

The tubular member 11 also has a handle portion 15 extending at angle with respect to the membrane contacting portion 13 to facilitate the manipulation by the obstetrician and the insertion of the member 11 inside the vagina of the woman W whenever necessary.

The tubular member 11 is advantageously made of a soft, unallergen plastic material. This hollow member which is preferably of constant diameter along its length, comprises a front end 17 at the extremity of the membrane contacting portion 13 and a rear end 19 at opposite extremity of the handle portion 15. As clearly illustrated in the accompanying drawings, the front end 17 is preferably splayed to ensure better contact with the foetal membranes 3 to be ruptured.

A piston 21 is movably mounted inside the tubular member 11. This piston 21 which can be made of a same plastic material as the tubular member 11, is sized and shaped to be tight enough inside the hollow member to create, when actuated, a vacuum sufficient to draw to a certain extent the foetal membranes 3 by succion inside the tubular member 11, as shown in FIG. 3. The piston 21 which is located in the membrane contacting portion 13 of the membrane 11 is manually actuated by a rod 23 having one end 25 fixed to or integrally projecting from the rear side of the piston 21 and the other end 27 extending outwardly of the tubular member 11 through the rear end 19 of this member.

Holding means preferably consisting of a ring 29 large enough to receive a finger of the obstetrician is advantageously fixed to the end 27 of the rod 23 to facilitate its manipulation. Of course, a hook or any similar holding means can be used instead of a ring, provided that it facilitates the manipulation of the rod 23.

Additional holding means which may also consist of a large ring 31, can be provided onto the external surface of the handle portion 15 of the tubular member 11 to facilitate handling and manipulation of the instrument 1. Of course, these means are not restricted to a particular ring but encompass any other means capable of performing the same portion, such as hooks or external handle.

In accordance with the very important aspect of the present invention, means are rigidly mounted in front of the piston 21 and close to the front end 17 of the member 11 inside this member for rupturing the foetal membranes 3 when these membranes are drawn inside the member 11 on actuation of the piston 21 with the rod 23.

Figure 2:
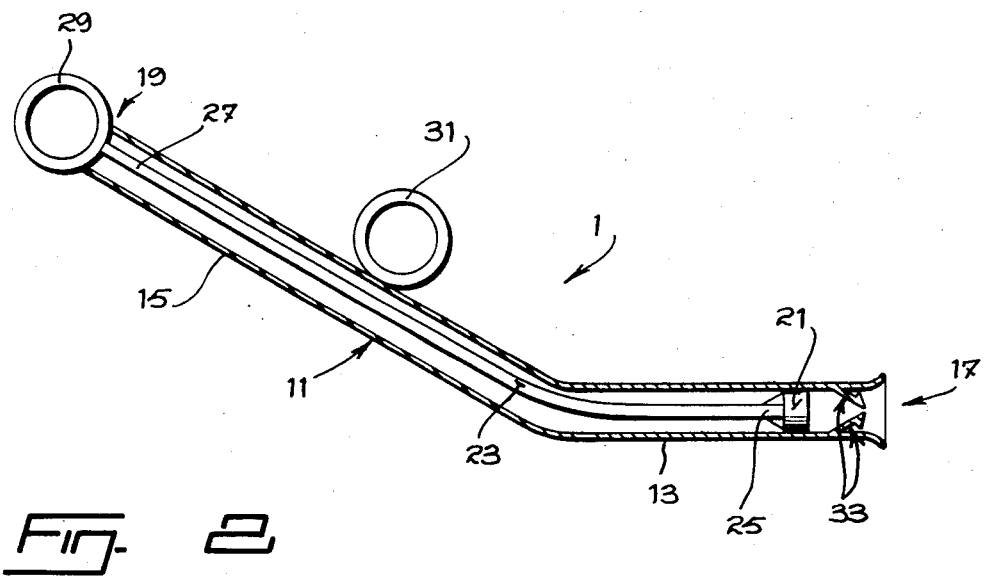
FIG. 2 is a side elevational view in cross-section of the obstetrical instrument shown in FIG. 1.

As shown in FIGS. 2 and 3, these means may advantageously comprise a pair of piercing pins inwardly and forwardly projecting inside the tubular member 11 to puncture and tear off the membranes 3 drawn in by the piston 21. As also shown in FIGS. 2 and 3, each of the piercing pins preferably has an arrow head-shaped tip 35 to facilitate the puncture and tear off of the membrane 3 drawn in by the piston 21.

As can now be easily understood, the instrument 1 previously described is particularly interesting in that it is very safe in use since the piercing pins 33 are rigidly mounted inside the tubular member 11 and thereby can never become into contact with the unborn baby B or with the internal tissue of the woman W. Since the front end 17 of the instrument 1 is relatively large in diameter, the risk to injure the unborn baby B when trying to rupture the membranes 3 are very small.

In addition, the operation of the instrument is very easy to reduce into practice.

As shown in FIG. 3b, the amniotic fluid 5 contained by the membranes 3 is of course pumped by the piston 21 inside the hollow member 11 as soon as the membranes 3 are ruptured. This particular feature makes the instrument 1 particular useful since it does allow the obstetrician to sample small amount of amniotic fluid 5 without this aminotic fluid having been in contact with the internal tissue of the woman W.

It should be noted that the present invention is by no way restricted to the description given hereinabove of a preferred embodiment thereof. As can be easily understood certain modifications or improvement can be made to the above described embodiment without departing from the spirit of the present invention as recited in the appended claims.

I claim:

1. An obstetrical instrument for rupturing in a safe and easy manner the foetal membranes of a pregnant woman in order to release the amniotic fluid contained in said membranes, said instrument comprising:
   an elongated tubular member having a front end with a blunt rim constituting a non-cutting engaging surface, and a rear end, said member being adapted to be inserted into the woman's vagina with the front end of said member in contact with the foetal membranes to be ruptured;
   a piston movably mounted inside said tubular member, said piston being tight enough to create, when actuated, a vacuum sufficient to draw to a certain extent the foetal membranes inside the tubular member;
   a rod for manually actuating the piston, said rod having one end fixed to said piston and the other end extending outwardly of the tubular member through the rear end thereof; and
   rupturing means fixedly mounted in front of the piston within said tubular member at a location inwardly spaced from and adjacent to said front end rim, for rupturing the foetal membranes when said membranes are drawn inside the tubular member on actuation of the piston with the rod.

2. The obstetrical instrument of claim 1, wherein:
   the tubular member is made of a rigid or semi-rigid material and is slightly bent along its length to define a membrane contacting portion insertable into the woman's vagina, and a handle portion extending at angle with respect to the membrane contacting portion;
   the piston is located in the membrane contacting portion of the member;
   the front end of said member is slightly splayed;

holding means are provided at the other end of the rod extending out of the member to facilitate its manipulation; and said means for rupturing the membranes comprise at least one piercing pin inwardly and forwardly projecting inside the tubular member to puncture and tear off the membranes drawn in by the piston.

3. The obstetrical instrument of claim 2, wherein:

the tubular member, the piston, the rod and the holding means of said rod are made of plastic material;

additional holding means made of plastic material and integral to the tubular member, are provided on the handle portion of said member to facilitate its manipulation; and said at least one piercing pin acting as said rupturing means has an arrow-head shaped tip.

4. The obstetrical instrument of claim 3, wherein:

said rupturing means comprise two arrow-head shaped piercing pins symmetrically positioned inside the tubular member.

5. The obstetrical instrument of claim 4, wherein:

said holding means and additional holding means consist of rings large enough to receive a finger.

6. The obstetrical instrument of claim 4, wherein:

said holding means and additional holding means consist of hooks engageable with a finger.

* * * * *